United States Patent [19]

Pettersson et al.

[11] Patent Number: 5,361,638

[45] Date of Patent: Nov. 8, 1994

[54] ARRANGEMENT FOR MEASURING MECHANICAL PROPERTIES OF A FOIL MATERIAL THROUGH USE OF AN EXCITATION UNIT THAT INCLUDES A LASER

[75] Inventors: Thorulf Pettersson; Jorma Anttila, both of Täby, Sweden

[73] Assignee: STFI, Stockholm, Sweden

[21] Appl. No.: 150,259

[22] Filed: Nov. 10, 1993

Related U.S. Application Data

[63] Continuation of Ser. No. 773,951, Jan. 3, 1992, abandoned.

[30] Foreign Application Priority Data

Mar. 30, 1990 [SE] Sweden ............... 9001162-8

[51] Int. Cl.⁵ ............................................. G01L 1/24
[52] U.S. Cl. ............................................. 73/800; 73/159; 356/432; 356/373
[58] Field of Search .............. 73/159, 788, 849, 800, 73/838; 356/432 T, 429, 430, 431, 32, 373

[56] References Cited

U.S. PATENT DOCUMENTS

| | | | |
|---|---|---|---|
| 3,605,486 | 9/1971 | Anderholm et al. | 73/788 |
| 4,246,793 | 1/1981 | Fairand et al. | 73/628 |
| 4,622,853 | 11/1986 | Leugers | 73/597 |
| 4,632,561 | 12/1986 | Rosencwaig et al. | 356/432 T |
| 4,952,063 | 8/1990 | Opsal et al. | 356/432 |
| 5,025,665 | 6/1991 | Keyes, IV et al. | 73/159 |

*Primary Examiner*—Hezron E. Williams
*Assistant Examiner*—Nashmiya N. Ashraf
*Attorney, Agent, or Firm*—Burns, Doane, Swecker & Mathis

[57] ABSTRACT

An arrangement for measuring mechanical properties of foil material (10), preferably paper. The arrangement includes a material excitation unit (12) and a material sensing detection unit (14). The two units are connected electrically to a common arithmetical unit (18). This unit is intended to register and convert electrical signals deriving from the two first mentioned units (12, 14) in a manner to produce final signals which represent the material properties to be measured. The excitation unit (12) includes a laser which, through electromagnetic radiation, is intended to generate in the gaseous atmosphere surrounding the material local transient gas-pressure pulses within variable surface zones which are well-defined geometrically, without the excitation unit coming into contact with the material. These gas pressure pulses cause the material (10) to stretch locally in the boundary regions of the zones, such stretching of the material being necessary to the measuring process. The detection unit (14) senses this stretching of the material, without coming into contact with the material, by detecting transient changes in these material zones.

20 Claims, 2 Drawing Sheets

ARRANGEMENT FOR MEASURING MECHANICAL PROPERTIES OF A FOIL MATERIAL THROUGH USE OF AN EXCITATION UNIT THAT INCLUDES A LASER

This application is a continuation of application Ser. No. 07/773,951, filed Jan. 3, 1992, now abandoned.

FIELD OF THE INVENTION

The present invention relates to an arrangement for measuring mechanical properties of foil material, e.g. paper, such as local strength and basis weight, with the aid of a material excitation unit which includes a laser, and also with the aid of a detection unit which senses excited material. The units are connected electrically to an arithmetical unit which registers and converts electric signals which derive from the two first mentioned units and which represent the starting values of the measuring process, for establishing the values of the final signals representative of the material properties to be measured.

BACKGROUND OF THE INVENTION

In paper manufacturing processes, it is very important that the mechanical properties of the paper be determined continuously, arid then particularly the strength of the paper in different directions, i.e. the strength anisotropy of the paper. The strength anistropy of paper can be determined when the elastic constants of the paper in different directions are known. It is known that these constants can be determined by subjecting the paper to static forces or to ultrasonic sound.

When the elastic constants are measured with the aid of ultrasonic sound, i.e. mechanical oscillations or vibrations of very high frequencies, e.g. frequencies which exceed 20 kHz, there is utilized the fact that the speed at which the sound propagates in different directions in the material is associated with the elastic constants of the material.

The aforesaid mechanical properties are preferably measured on-line, i.e. directly on the paper web in the paper manufacturing process, while advancing the web continuously, although said properties can also be determined off-line, i.e. on paper samples in a laboratory. Before it is possible to take on-line measurements, it is necessary to solve a number of complicated technical problems which are associated with the specific properties of the material being measured and with prevailing measuring and manufacturing conditions. In this respect, it is necessary to take into account the relatively high speed of the paper web—up to 20 meters per second—and, for instance, the fact that movements are liable to occur in the paper web during its manufacture—web flutter—and that an intensive acoustic noise is generated. Thus, this high noise level coupled with the difficulties associated with exciting the material with ultrasonic waves of sufficiently high energy levels makes on-line measuring of the technical properties of paper very difficult to carry-out with the aid of known technology.

U.S. Pat. No. 4,291,577 describes an arrangement in which a contacting measuring device is used for ultrasound measuring purposes. This measuring device includes a transmitter in the form of a piezoelectric element which generates mechanical oscillations of frequency 20 kHz. Longitudinal high-frequency waves are generated in the excited paper in this way, through the contacting piezoelectric element, these waves propagating in different directions in the material in the plane of the material web. A receiver, which also consists of a contacting piezoelectric element, is located at a predetermined distance from the transmitter, thereby enabling the phase velocity of the ultrasonic sound to be calculated, this velocity being related to the modulus of elasticity of the paper. This arrangement, however, is highly sensitive to external influences, for instance the aforementioned noise, uncontrollable variations in the distance travelled by the web, etc. It will also be evident to all those skilled in this art that an arrangement which utilizes movable parts which are in direct contact, such as the arrangement illustrated in the aforesaid U.S. Pat. No. 4,291,577, will also incur other serious drawbacks. For instance, the known arrangement is relatively complicated, due to its construction, and consequently malfunctions are very likely to occur. Furthermore, it is not certain that the transmitter/receiver will remain in physical contact with the paper web at high web speeds and with paper webs of high surface roughness. The web-contacting parts of the arrangement are also liable to damage the paper.

It is also known to apply the principle of contactless registration of the propagation of ultrasonic sound waves for the purpose of measuring the mechanical strength of a stationary or a moving material. One such method is described, for instance, in Swedish Patent Application No. 8017/70 (Publication No. 359 962). The complicated relationships which prevail between the measured parameters and the elastic paper constants when practicing this method, and also the sensitivity of the method to uncontrollable variations in air flows adjacent the material web, make it difficult to apply this method in practice for on-line measuring processes.

It is also known to utilize bending waves, so-called Lamb's waves to indicate the thickness of and the faults in sheet-like or foil materials. Arrangements of this kind are described in U.S. Pat. Nos. 2,536,128 and 3,210,120, for instance. With these arrangements, energy from a radiation source is fed into sheet-like or foil material at a given angle of incidence, with the aid of a coupling liquid, thereby enabling the phase velocity of the bending wave to be measured. A method which is based on the use of a contact liquid is not suitable for use when measuring or determining the properties of, for instance, paper, for obvious reasons.

U.S. Pat. No. 4,180,324 teaches another method of measuring material properties by studying wave movements originating from an excitation location in the form of ultrasonic sound. Although this method can be used, in principle, for measuring the strength of foil material in a punctiform fashion, it can only be used to determine the strength of the material in its z-direction, i.e. a direction transversely through the material at right angles to the surface thereof. Another distinguishing feature when using the novel inventive arrangement, in addition to not studying the propagation of ultrasonic waves, is that the novel construction affords the possibility of measuring material strength locally in different directions in the plane of the material. This is achieved by utilizing the discovered changeable relationship between the generated macroscopic elastic extension or stretch of the material and the strength of the material in different directions, through geometric configuration and orientation of the excitation zones used.

Another known method described in U.S. Pat. No. 4,674,332 can, in principle, be configured for non-contacting on-line measuring processes. In this case, the ultrasonic sound waves are generated thermally with the aid of laser light. This measuring technique, however, similar to the method according to U.S. Pat. No. 4,291,577, requires accurate determination of running times or phase changes over well-defined travel distances, in order to establish the phase-velocity of the ultrasonic waves generated and propagating in the material. Such measurements are difficult to make accurately, particularly on-line, and the result obtained is also difficult to relate directly to strength properties which are significant to the paper manufacturer, particularly when measuring the properties of paper. One reason for this is that the measurement values obtained constitute the mean values measured over relatively long travel distances, normally tens of centimeters when measuring in the plane of the paper. The occurrence of local minimum values can have a decisive significance on the relationship between the paper strength measured with ultrasonic sound and the paper testing result obtained in the laboratory when using conventional paper testing procedures.

OBJECTS AND SUMMARY OF THE INVENTION

One object of the present invention is to provide an arrangement of the kind described in the introduction which will eliminate the drawbacks of known techniques and enable the intended measurements to be established. The arrangement shall thus be constructed so that no movable parts which require maintenance and which readily cause malfunctions to occur or give rise to signal noise will come into contact with the paper web. Neither shall the construction give rise to contact problems in relation to the paper, irrespective of the speed or surface roughness of the web. Neither shall the invention be based on measuring the phase velocity of the generated ultrasonic which propagates in different directions in the material, since this type of measuring process is difficult to perform on-line with sufficient accuracy. The invention shall also enable material properties to be registered locally within very small surface elements, or areas, e.g. areas in the order of some square millimeters. This enables the static local strength and pulp distribution to be established, together with occurrent local extreme values, something which cannot be achieved on-line with the aid of known technical measuring techniques. Finally, it shall also be possible during the measuring process to register the anisotropy of the mechanical properties which are associated with the angular orientation of the cellulose fibers, when measuring paper for instance.

An arrangement of the kind described in the introductory paragraph and which fulfils the aforesaid requirements is, in accordance with the invention, characterized primarily in that the excitation unit functions to generate local transient gas-pressure pulses in the gaseous atmosphere which surrounds the material, normally atmospheric air, with the aid of electromagnetic radiation delivered by the laser and through the generation of local plasma within at least one geometrically well-defined surface zone on the material which is determined by the geometric extension of the surface region irradiated with laser light, without the material being in contact with the excitation unit, there-with to produce local transient stretching of the material in the limit border of the zone necessary for the measuring process concerned, and in that the detection unit functions to detect local stretching of the material by direct or indirect detection of changes in said material zone, without coming into contact with said material.

The invention provides particular, novel and unique possibilities of frequent measuring on-line local variations in the strength and in the mass distribution of foil material. For instance, the invention enables the strength and/or basis weight of the foil material to be measured at areas having a size smaller than some square millimeters, a thousand times per second.

The electromagnetic radiation delivered by the laser, this radiation consisting of coherent pulsed short-wave radiation, is caused to produce a transient, very high overpressure in a small geometrically well-defined gas zone located in the immediate vicinity of the surface of the foil material, via local plasma generation. The pressure pulse generated in this way has a very rapid lapse, e.g. a lapse on the microsecond level. The pressure pulse used to excite the material must have an extremely short rise time, so that essentially only that part of the material surface which is located within the excitation zone is able to move within the time space immediate interest. The intended effect, which forms the basis of the inventive measuring process, i.e. transient local stretching of the material, will not otherwise be achieved. It will be noted that the duration of the pressure pulse in practice is not determined by the duration of the laser pulse when the laser pulses are shorter than 100 ns, but is instead determined by the geometric extension of the excitation zone and the properties of the plasma generated. For instance, a circular excitation zone having a radius of one mm (1 mm) gives the generated pressure pulse a duration on the microsecond level, despite the fact that the duration of the laser pulse is on a nanosecond level. It can be mentioned in summary that practical paper-measuring tests carried out by us showed that it is possible to generate pressure pulses of sufficiently short rise times when practicing the afore-described method. When applying a power density of $10^6$ W/cm$^2$ in the excitation zone, it has been found possible to achieve the requisite pressure-pulse generation without appreciably heating the paper material, even when the same point on a stationary paper web is repeatedly excited.

Tests have shown that the magnitude of the excitation-induced stretch is contingent on the geometric extensions of the excitation zone in different directions in the plane of the paper, and on the tensile stiffness of the paper in said different directions. The basis weight or surface weight of the paper also influences the stretch progress coupled to the mass inertia of the material accelerated within the excitation zone. The total area of the excitation zone and the amplitude of the transient excitation pressure will also, of course, influence the magnitude of stretch or tensile extension, although these parameters can be considered to be selectable and measurable parameters for a given measuring configuration. By changing the geometry and/or orientation of the excitation zone, it has been found possible to vary the influence of the material properties to be measured on the resultant registered stretch and, in this way, to provide also information relating to the strength anisotropy. In practice, this can be done, for instance, sequentially by exciting and rotating a rectangular excitation zone or by simultaneous excitation at several points and using excitation zones of different configuration or orientation. Many different possibilities in this regard are afforded by the aforesaid basic principle.

Orientation of an elongated rectangular excitation zone with its long axis in the direction, the x-direction, in which the foil material exhibits low tensile stiffness will result in a small degree of stretch. Thus, the influence exerted by the high tensile strength of the material in the y-direction is relatively large. On the other hand, a large degree of stretch is obtained when the excitation zone is oriented with its long axis in the y-direction, i.e. the influence exerted by the low tensile strength of the material in the x-direction is relatively large. It should be noted that when measuring paper samples, a difference in tensile stiffness in said two directions which includes a factor of 3 (three) may sometimes be obtained.

The basis weight of the material, the influence of which on stretching of the material depends on the total surface area of the excitation zone but, in principle, is independent of the orientation of the excitation zone, can also be read from the transient stretching process. The influence of basis weight is particularly pronounced in the initial phase of the stretching process, which corresponds to the high frequency components in the signal from the detection unit.

In distinction to basis weight, the mechanical strength of the material influences mainly the low frequency components in the signal from the detection unit, which in the time plane is corresponded by the time interval in which the material present within the excitation zone is retarded.

The frequency band between the aforesaid low and high frequency range provides supplementary information concerning prevailing energy losses which occur in conjunction with local stretching of the material.

The aforesaid relationships, i.e. varying degrees of sensitivity to different mechanical properties of the material within different frequency bands/time intervals coupled with the geometric configuration and orientation of the excitation zones, are utilized in conjunction with the inventive measuring arrangement for the purpose of calculating the values of the material properties in question.

BRIEF DESCRIPTION OF THE DRAWING FIGURES

The invention will now be described in more detail with reference to preferred exemplifying embodiments thereof and with reference to the accompanying drawings, in which FIG. 1 is a plan view from one side of a measuring arrangement constructed in accordance with the principles of the invention and disposed adjacent a movable paper web;

FIG. 2 illustrates a measuring situation in which the material is excited sequentially at one single point thereon with a varying, geometrically configured excitation zone, where detection of the transient stretching process is detected with the aid of a pressure-responsive sensor; and FIG. 3 illustrates measuring situations in which the material is excited simultaneously at two points thereon with excitation zones of different geometrical configuration, where detection of the transient stretching process is effected with the aid of optical sensors.

DETAILED DESCRIPTION OF THE INVENTION

Figure 1:
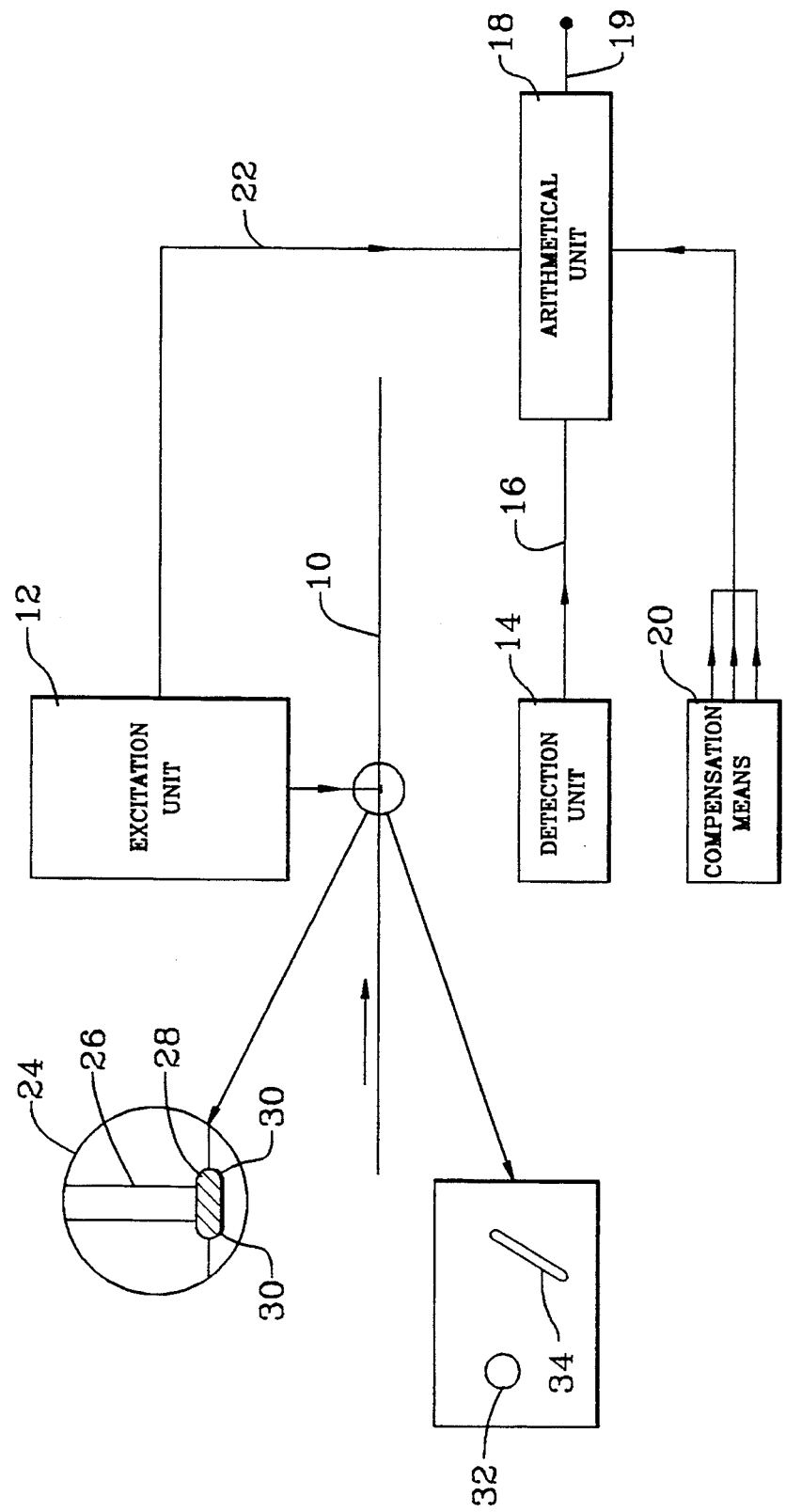

FIG. 1 is a block schematic which illustrates one embodiment of the novel measuring arrangement located adjacent a paper web 10 which is advanced continuously in the arrowed direction, and also illustrates the main principles of the invention. Both excitation and detection are effected in a contactless manner with respect to the paper web 10, by means of an excitation unit 12 positioned above the web and a detection unit 14 positioned beneath said web. The detection unit 14 is connected to an arithmetical unit 18 having an output 19, by means of a signal conductor 16. The arithmetical unit includes a computer or microprocessor provided with adaptation means (not shown) and being suitably constructed in a manner such as to calculate the determinable local strength and basis weight of the material on the measuring occasion on the basis of the prevailing transient stretching process as seen in the time or frequency plane, and also to compensate these calculated values in respect of temperature, moisture and thickness variations, if desired in a known manner with the aid of compensation means 20. This enables numerical values corresponding to the material properties concerned to be established under standardized measuring conditions. The arithmetical unit 18 also receives on a further signal line 22 a reference signal which represents the intensity of the radiation delivered by the excitation unit 12.

FIG. 1 also shows separately an enlarged part 24 in the vicinity of the region in which the laser beam 26 delivered by the excitation unit 12 impinges on the paper web. This enlarged part of FIG. 1 shows a plasma zone 28 and local stretching in zone 30 of the material web caused by the generation of local transient overpressure in the boundary region of the plasma zone 28 in the direction of the material surface.

Other forms of the actual excitation zone 32 and 34 respectively are also shown in an enlarged view in FIG. 1. As shown in the Figure, the zones may have a circular or an elongated rectangular shape for instance.

The illustrated arrangement includes the excitation unit 12, a so-called EXCIMER-laser. This laser is able to generate short pulses of shortwave light radiation of sufficiently high energy to effect local plasma generation. As before mentioned, this is a prerequisite for generating the intended pressure pulse and carrying out the measuring process. Plasma generation requires a very high power density, normally a power density in excess of $10^4$ W/cm$^2$.

Figure 2:
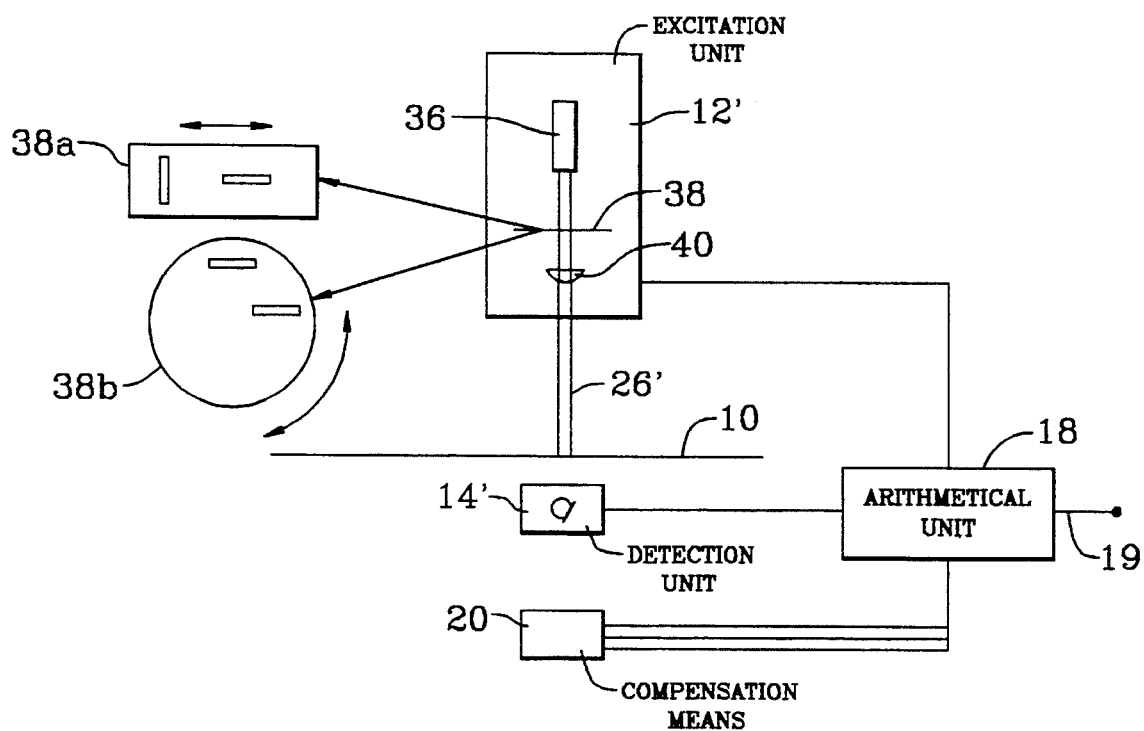

In the case of the embodiment illustrated in FIG. 2, the excitation unit 12' operates with a single laser beam 26'. This beam is generated by a laser 36 through an apertured diaphragm 38 and a lens 40. The FIG. 2 embodiment includes two different types of diaphragms 38a and 38b which can be used to create excitation zones in different directions in the material. The upper diaphragm 38a has two apertures which diaphragm the laser beam 26' when displaced in the arrowed direction. Similar diaphragming of the beam is also achieved with the bottom, alternative diaphragm 38b, which is rotatable.

The detecting unit 14' of the FIG. 2 embodiment comprises a pressure-responsive sensor. This sensor receives requisite information concerning the transient stretch or elastic elongation of the material when the material element within an excitation zone is accelerated upon the occurrence of stretch and therewith gives rise to a pressure wave in the surrounding air. The progress of the thus generated pressure wave provides the information concerning the transient stretching process required for calculating the mechanical properties to be ascertained.

Figure 3:
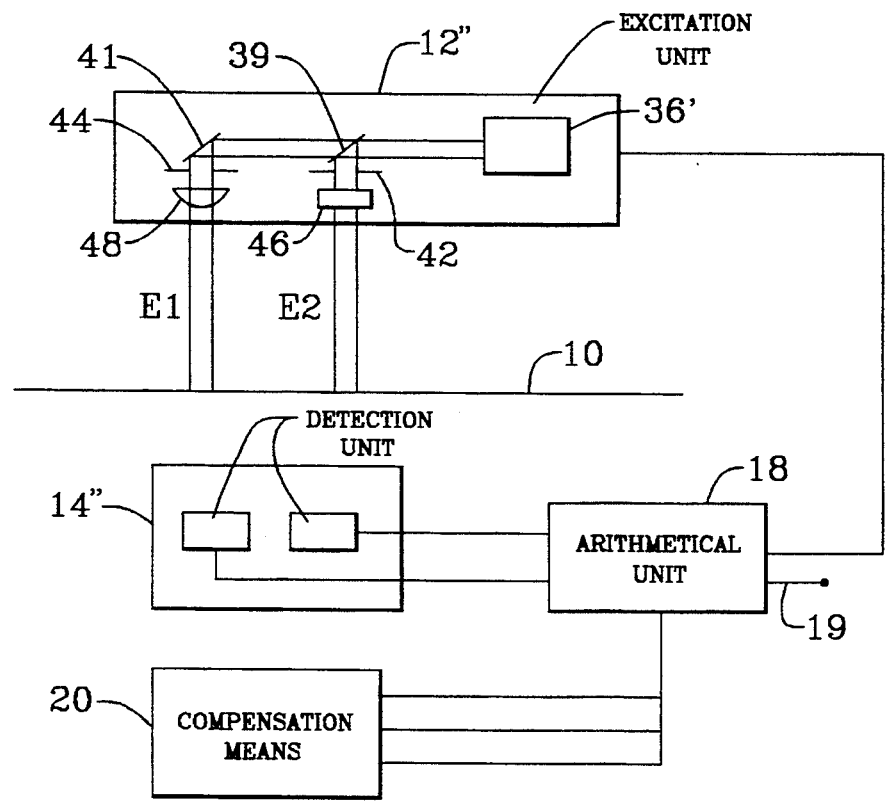

FIG. 3 illustrates another embodiment of the inventive arrangement and illustrates the manner in which the novel measuring arrangement operates when the beam delivered by a laser 36' is divided and exits from the excitation unit 12" in the form of two, simultaneously operating laser beams E1 and E2. The laser beam is split in the excitation unit 12" into said two laser beams E1 and E2 with the aid of reflecting mirrors 39, 41, apertured diaphragms 42, 44 and lenses 46, 48—preferably cylindrical lenses. These beams are directed onto the paper web 10 and give rise simultaneously to pressure pulses in two differently oriented excitation zones. In this case, detection is effected on opposite sides of the paper web 10 at an appropriate distance from respective excitation locations, and is achieved with the aid of an optical position sensing detecting unit 14".

In the aforedescribed embodiments, there is obtained from respective arithmetical units an output signal which gives information concerning the local strength and basis weight of the paper web 10.

It will be obvious to one of normal skill in the art that the fundamental principle of the novel, inventive measuring arrangement demonstrated in the aforegoing can be modified in different ways with respect to the design of details within the scope of the following claims. It also lies within the scope of the invention to distribute the laser beams used with the aid of fiber optics,- therewith enabling the measuring arrangement to be placed readily available at desired distances from the paper web concerned. Furthermore, the novel measuring arrangement can be readily arranged for so-called traversing. This implies that the arrangement can be moved transversely to the feed direction of the paper machine, even during operation. As an alternative to the detection unit illustrated in FIG. 1, there can be used a known detection arrangement for registering, for instance, local changes which result from elongation or stretching of the material.

What is claimed is:

1. An arrangement for measuring mechanical properties of foil material surrounded by a gaseous atmosphere, comprising: excitation means which includes a laser for influencing the material by generating local transient gas-pressure pulses in the gaseous atmosphere surrounding the material with the aid of electromagnetic radiation delivered by the laser via local plasma generation within at least one geometrically well-defined surface zone of the material, the surface zone being determined by a geometric extension of a surface area irradiated by the laser, the excitation means producing local transient stretching of the material in boundary regions of the surface zone without the material coming into contact with the excitation means, detection means for detecting changes in said at least one surface zone of the material influenced by the excitation means without coming into contact with the material, said excitation means and said detection means being connected electrically to arithmetical means for registering and converting electrical signals derived from the excitation means and the detection means, the electrical signals representing output values of a measuring process for establishing values of signals representative of properties to be measured, the transient stretching of the material being requisite to the measuring process.

2. An arrangement according to claim 1, wherein the detection means detects changes in elongation of the material.

3. An arrangement according to claim 1, wherein the laser in the excitation means is a pulsed gas laser.

4. An arrangement according to claim 1, wherein the excitation means simultaneously excites the material in more than one point on the material.

5. An arrangement according to claim 4, wherein the excitation means excites the material within excitation zones of different geometrical configuration.

6. An arrangement according to claim 1, wherein the detection means sequentially detects material changes in more than one point.

7. An arrangement according to claim 1, wherein the detection means includes at least one sensor which is responsive to a pressure wave produced as a result of the transient stretching of the material.

8. An arrangement according to claim 1, wherein said excitation means includes two reflecting mirrors which split a laser beam produced by said laser into two laser beams, the detection means including at least one position-sensing optical sensor.

9. An arrangement according to claim 1, wherein the arithmetical means compensates for prevailing disturbing influences on a relationship between the mechanical properties to be measured and a measured local transient material-stretching process which result from variations in temperature, moisture and thickness of the material during the measuring process.

10. An arrangement according to claim 2, wherein the detection means detects density changes.

11. An arrangement according to claim 3, wherein the pulsed gas laser is an EXCIMER-laser.

12. An arrangement according to claim 1, wherein a plurality of points on the material are sequentially excited by the excitation means.

13. An arrangement according to claim 1, wherein the excitation means excites the material with excitation zones of different orientation.

14. An arrangement according to claim 1, wherein the detection means simultaneously detects material changes at more than one point.

15. An arrangement according to claim 6, wherein the detection means includes at least one sensor which is responsive to a pressure wave produced as a result of the transient stretching of the material.

16. An arrangement according to claim 14, wherein the detection means includes at least one sensor which is responsive to a pressure wave produced as a result of the transient stretching of the material.

17. An arrangement according to claim 6, wherein said excitation means includes two reflecting mirrors which split a laser beam produced by said laser into two laser beams, the detection means including at least one position-sensing optical sensor, 18. An arrangement according to claim 14, wherein said excitation means includes two reflecting mirrors which split a laser beam produced by said laser into two laser beams, the detection means including at least one position-sensing optical sensor.

19. An arrangement according to claim 7, wherein the arithmetical means compensates for prevailing disturbing influences on a relationship between the mechanical properties to be measured and a measured local transient material-stretching process which result from variations in temperature, moisture and thickness of the material during the measuring process.

20. An arrangement according to claim 8, wherein the arithmetical means compensates for prevailing disturbing influences on a relationship between the mechanical properties to be measured and a measured local transient material-stretching process which results from variations in temperature, moisture and thickness of the material during the measuring process.

* * * * *